United States Patent
Toenjes et al.

(10) Patent No.: US 9,686,987 B2
(45) Date of Patent: Jun. 27, 2017

(54) METHOD FOR INHIBITING CONIDIAL GERMINATION AND MYCELIAL GROWTH OF FUNGI SYMBIOTICALLY ASSOCIATED WITH BARK BEETLES

(71) Applicant: Montana State University—Billings, Billings, MT (US)

(72) Inventors: Kurt A. Toenjes, Billings, MT (US); David K. Butler, Billings, MT (US); Joy Goffena, Roundup, MT (US)

(73) Assignee: Montana State University—Billings, Billings, MT (US)

( * ) Notice: Subject to any disclaimer, the term of this patent is extended or adjusted under 35 U.S.C. 154(b) by 0 days.

(21) Appl. No.: 15/208,312

(22) Filed: Jul. 12, 2016

(65) Prior Publication Data

US 2017/0000126 A1    Jan. 5, 2017

Related U.S. Application Data

(63) Continuation-in-part of application No. 14/751,617, filed on Jun. 26, 2015, now Pat. No. 9,426,992.

(51) Int. Cl.
*A01N 43/78* (2006.01)

(52) U.S. Cl.
CPC .................................. *A01N 43/78* (2013.01)

(58) Field of Classification Search
CPC .................................................... A01N 43/78
See application file for complete search history.

(56) References Cited

U.S. PATENT DOCUMENTS

RE43,615 E    8/2012  Toenjes et al.

OTHER PUBLICATIONS

Six, D. L. and T. D. Paine (1998) The effects of mycangial fungi on development and emergence of Dendroctonus ponderosee and D. jeffreyi. Environmental Entomology. 27: 1393-14.
Bleiker, K. and D.L. Six (2007) Dietary benefits of fungal associates to an eruptive herbivore: potential implications of multiple associates on host population dynamics. Envi. Sci 108(6):2504-2509.
Galagan, J. E., Henn, M. R., Ma, L., Cuomo C. A., and B. Birren (2005) Genomics of the fungal kingdom: insights into eukaryotic biology. Genome Research. 15(12): 1620-1631.
Schmalreck et al. (2014) Phylogenetic relationships matter: antifungal susceptibility among clinically relevant yeasts. Antimicrobial Agents and Chemotherapy. 58(3):1575-1585.
Degterev, A., A. Lugovsky, M. Cardone, B. Mulley, G. Wagner, T. Mitchison and J. Yuan. 2001. Identification of small-molecule Inhibitors of Interaction between the BH3 domain and Bcl-XL. Nature Cell Biol. 3: 173-182.
Toejnes, K.A., at al. (2005) Small-molecule inhibitors of the budded-to-hyphal-form transition in the pathogenic yeast Candida albicans. Antimicrobial Agents and Chemotherapy. 49: 963-972.
Toenjes K.A., Stark B.C., Brooks K.M. and D.I. Johnson (2009) Inhibitors of cellular signaling are cytotoxic or block the budded-to-hyphal transition in the pathogenic yeast *Candida albicans*. J Med Microbiol 58: 779-790.
Six D., Ecological and evolutionary determinants of bark beetle-fungus symbioses. Insects 3: 339-366.
Six, D. L. and T. D. Paine (1998) The effects of mycangial fungi on development and emergence of Dendroctonus ponderosse and D. jeffreyl. Environmental Entomology. 27: 1393-14.
Six, D.L. and M.J. Wingfield (2011) The Role of Phytopathogenicity in Bark Beetle-Fungus Symbioses: A Challenge to the Classic Paradigm. Annu. Rev. Entomol. 56: 255-272.
Diguistini et al. (2011) Genome and transcriptome analyses of the mountain pine beetle-fungal symbiont Grosmannia clavigera, a lodgepole pine pathogen. Proc. Natl. Academ. Sci. 108(6): 2504-2509.
Galagan, J.E., Henn, M. R., Ma, L., Cuomo C. A., and B. Birren (2005) Genomics of the fungal kingdom: Insights into eukaryotic biology, Genome Research. 15(12): 1620-1631.
Schmalreck et al. (2014) Phylogenetic relationships matter: antifungal susceptibility among clinically relevant yeasts. Antimicrobial Agens and Chemotherapy, 58(3):1575-1585.
Degterev, A., A. Lugovsky, M. Cardone, B. Mulley, G. Wagner, T. Mitchison and J. Yuan, 2001. Identification of small-molecule inhibitors of interaction between the BH3 domain and Bcl-XL. Nature Cell Biol. 3: 173-182.
Fedorova, N.D., J. H. Badger, G. D. Robson, J. R. Wortman and W. C. Nierman 2005. Comparative analysis of programmed cell death pathways in filamentous fungi. BMC Genomics 6: 177-191.
Toejnes, K.A., et al. (2005) Small-molecule inhibitors of the budded-to-hyphal-form transition in the pathogenic yeast *Candida albicans*. Antimicrobial Agents and Chemotherapy. 49: 963-972.

*Primary Examiner* — Samantha Shterengarts
(74) *Attorney, Agent, or Firm* — Antoinette M. Tease

(57) ABSTRACT

A method for controlling conidial germination and mycelial growth in fungi comprising contacting a fungal cell with anti-fungal small molecules in an amount effective to reduce or inhibit conidial germination and mycelial growth. A method for controlling bark beetle infestations of pine trees comprising contacting one or more fungal cells with anti-fungal small molecules in an amount effective to reduce or inhibit conidial germination and mycelial growth. The anti-fungal small molecules are 5-(p-Bromobenzylidine)-α-isopropyl-4-oxo-2-thioxo-3-thiozolidineacetic acid, 2-[5-(4-chlorobenzylidene)-4-oxo-2-thioxo-1,3-thiazolidin-3-yl]-3-methylbutanoic acid, 2-[5-(4-hydroxybenzylidene)-4-oxo-2-thioxo-1,3-thiazolidin-3-yl]pentanoic acid, [5-(4-isopropylbenzylidene)-4-oxo-2-thioxo-1,3-thiazolidin-3-yl] acetic acid or 2-[5-(2-chlorobenzylidene)-4-oxo-2-thioxo-1, 3-thiazolidin-3-yl]pentanoic acid. The species of the fungal cell is selected from a group that has an obligate symbiosis with the mountain pine beetle (*Dendroctonus ponderosae*) and the western pine beetle (*Dendroctonus brevicomis*).

32 Claims, 15 Drawing Sheets

BH3I-1

BH3I-1-12

BH3I-1-68

BH3I-1-69

BH3I-1

BH3I-1-12

BH3I-1-66

BH3I-1-68

BH3I-1-69

METHOD FOR INHIBITING CONIDIAL GERMINATION AND MYCELIAL GROWTH OF FUNGI SYMBIOTICALLY ASSOCIATED WITH BARK BEETLES

CROSS-REFERENCE TO RELATED APPLICATION

This application is a continuation-in-part of U.S. patent application Ser. No. 14/751,617 filed on Jun. 26, 2016, the contents of which are incorporated herein by reference.

STATEMENT REGARDING FEDERALLY SPONSORED RESEARCH OR DEVELOPMENT

This invention was made with government support under Award No. PG15-66120-01 to Montana State University, Sub-Award No. G119-15-W4747 to Montana State University-Billings, awarded by the National Science Foundation. The government has certain rights in the invention.

BACKGROUND OF THE INVENTION

1. Field of the Invention

The present invention relates generally to the field of molecular biology, and more specifically, to a method for inhibiting conidial germination and mycelial growth of fungi that live symbiotically with various species of bark beetles.

2. Description of the Related Art

The present invention addresses the need to control infestations of coniferous trees by different species of bark beetles. Bark beetles, such as the mountain pine beetle *Dendroctonus ponderosae* and the western pine beetle *Dendroctonus brevicomis*, are responsible for killing large numbers of coniferous trees over vast areas of western North America. Indeed, beetle outbreaks are the leading cause of pine tree mortality in North America, and since the outbreak began in the late 1990s, approximately 45 million acres of pine trees have been killed in United States alone.

Bark beetles colonize pine trees as a natural part of their life cycle. During mid-summer, so-called "pioneer" beetles initiate tree colonization by boring through the bark and releasing pheromones that attract additional male and female beetles to a tree. The congregating beetles then mate, excavate an egg chamber within the phloem layer, lay eggs and die. After hatching, the larval progeny develop within the tree (carving out a system of tunnels as they feed on the sapwood) and emerge the following summer as adults. Many bark beetles colonize weak or dying trees; however, in the current outbreak, mountain pine beetles are colonizing and killing healthy trees.

Most species of bark beetles are host to a variety of fungal species from the genera *Grosmannia*, *Ophiostoma*, *Ceratocystiopsis* and *Ceratocystis* (1). Many of these fungal species have an obligate symbiotic relationship with bark beetles; that is, the fungi are required for the survival of the host bark beetle, most likely by providing access to tree nutrients (2,3,4). The beetles carry their symbiotic fungi as conidia in mycangia, specialized structures located on their exoskeleton. During colonization of a pine tree, the bark beetles passively introduce fungal conidia to the tree interior. Through conidial germination and mycelial growth, the fungi are able to invade phloem layer and sometimes also the xylem of the tree, discoloring the wood and disrupting water flow in the tree. It is not clear whether the fungi have a direct causal role in tree death (through mycelial invasion of the wood, for example) or whether they contribute indirectly to tree death through their symbiotic relationship with the beetles. In any case, the chemical inhibition of fungal growth—that is, the inhibition of conidial germination and/or mycelial growth—may provide a novel means of managing, controlling or limiting bark beetle infestations of pine trees.

The present invention is based on the unexpected discovery that the small molecule 5-(p-Bromobenzylidine)-α-isopropyl-4-oxo-2-thioxo-3-thiozolidineacetic acid (hereafter referred to as "BH3I-1") and four structurally related molecules, 2-[5-(4-chlorobenzylidene)-4-oxo-2-thioxo-1,3-thiazolidin-3-yl]-3-methylbutanoic acid (hereafter referred to as "BH3I-1-12"), 2-[5-(4-hydroxybenzylidene)-4-oxo-2-thioxo-1,3-thiazolidin-3-yl]pentanoic acid (hereafter referred to as "BH3I-1-66"), [5-(4-isopropylbenzylidene)-4-oxo-2-thioxo-1,3-thiazolidin-3-yl]acetic acid (hereafter referred to as "BH3I-1-68") and 2-[5-(2-chlorobenzylidene)-4-oxo-2-thioxo-1,3-thiazolidin-3-yl]pentanoic acid (hereafter referred to as "BH3I-1-69"), inhibit the conidial germination and mycelial growth of fungal species that have an obligate symbiotic relationship with the mountain pine beetle (*Dendroctonus ponderosae*) and the western pine beetle (*Dendroctonus brevicomis*). The fungal species inhibited by BH3I-1, BH3I-I-12, BH3I-1-66, BH3I-1-68 and BH3I-1-69 include *Grosmannia clavigera* (symbiont of mountain pine beetle), *Ophiostoma montium* (symbiont of mountain pine beetle) and *Ceratocystiopsis brevicomi* (symbiont of western pine beetle).

The inventors do not think the inhibitory activity of BH3I-1 against bark beetle fungal symbionts is an obvious discovery in light of prior art. The inventors previously found that BH3I-1 inhibits morphogcnesis (i.e., the yeast-to-filamentous growth transition) in *Candida ulbicans* (5). *C. albicans* and the bark beetle fungal symbionts share only a distant evolutionary history. Comparative genomic analyses have placed *C. albicans* and *G. clavigera* (the mountain pine beetle symbiont) in different taxonomic subphyla with a most recent common ancestor of approximately 350 million years ago (6,7). Because it has been shown that antifungal susceptibility can vary widely even among species of the same genus (8), there is no basis to expect that an inhibitory molecule will be active on such evolutionarily divergent fungi as *C. albicans* and the bark beetle fungal symbionts.

BRIEF SUMMARY OF THE INVENTION

The present invention is a method for controlling conidial germination and mycelial growth in fungi comprising contacting a fungal cell with an anti-fungal small molecule in an amount effective to reduce or inhibit conidial germination and mycelial growth, wherein the anti-fungal small molecule is either 5-(p-Bromobenzylidine)-α-isopropyl-4-oxo-2-thioxo-3-thiozolidineacetic acid, 2-[5-(4-chlorobenzylidene)-4-oxo-2-thioxo-1,3-thiazolidin-3-yl]-3-methylbutanoic acid, 2-[5-(4-hydroxybenzylidene)-4-oxo-2-thioxo-1,3-thiazolidin-3-yl]pentanoic acid, [5-(4-isopropylbenzylidene)-4-oxo-2-thioxo-1,3-thiazolidin-3-yl]acetic acid or 2-[5-(2-chlorobenzylidene)-4-oxo-2-thioxo-1,3-thiazolidin-3-yl]pentanoic acid, and wherein the species of the fungal cell is *Grosmannia clavigera*. In an alternate embodiment, the present invention is a method for controlling conidial germination and mycelial growth in fungi comprising contacting a fungal cell with an anti-fungal small molecule in an amount effective to reduce or inhibit conidial germination and mycelial growth, wherein the anti-fungal small molecule is either 5-(p-Bromobenzylidine)-α-isopropyl-4-oxo-2-thioxo-3-thiozolidineacetic acid, 2-[5-(4-chlorobenzylidene)-4-oxo-2-thioxo-1,3-thiazolidin-3-yl]-3-methylbutanoic acid, 2-[5(4-hydroxybenzylidene)-4-oxo-7-thioxo-1,3-thiazolidin-3-yl]pentanoic acid, [5-(4-isopropylbenzylidene)-4-oxo-2-thioxo-1,3-thiazolidin-3-yl] acetic acid or 2-[5-(2-chlorobenzylidene)-4-oxo-2-thioxo-1,3-thiazolidin-3-yl]pentanoic acid, and wherein the species of the fungal cell is *Ophiostoma montium*. In another alternate embodiment, the present invention is a method for controlling conidial germination and mycelial growth in fungi comprising contacting a fungal cell with an anti-fungal small molecule in an amount effective to reduce or inhibit conidial germination and mycelial growth, wherein the anti-fungal small molecule is either 5-(p-Bromobenzylidine)-α-isopropyl-4-oxo-2-thioxo-3-thiozolidineacetic acid, 2-[5-(4-chlorobenzylidene)-4-oxo-2-thioxo-1,3-thiazolidin-3-yl]-3-methylbutanoic acid, 2-[5-(4-hydroxybenzylidene)-4-oxo-2-thioxo-1,3-thiazolidin-3-yl]pentanoic acid, [5-(4-isopropylbenzylidene)-4-oxo-2-thioxo-1,3-thiazolidin-3-yl] acetic acid or 2-[5-(2-chlorobenzylidene)-4-oxo 2-thioxo-1,3-thiazolidin-3-yl]pentanoic acid, and wherein the species of the fungal cell is *Ceratocystiopsis brevicomi*.

The present invention is a method for controlling bark beetle infestations of pine trees comprising contacting one or more fungal cells with an anti-fungal small molecule in an amount effective to reduce or inhibit conidial germination and mycelial growth, wherein the anti-fungal small molecule is either 5-(p-Bromobenzylidine)-α-isopropyl-4-oxo-2-thioxo-3-thiozolidineacetic acid, 2-[5-(4-chlorobenzylidene)-4-oxo-2-thioxo-1,3-thiazolidin-3-yl]-3-methylbutanoic acid, 2-[5-(4-hydroxybenzylidene)-4-oxo-2-thioxo-1,3-thiazolidin-3-yl]pentanoic acid, [5-(4-isopropylbenzylidene)-4-oxo-2-thioxo-1,3-thiazolidin-3-yl] acetic acid or 2-[5-(2-chlorobenzylidene)-4-oxo-2-thioxo-1,3-thiazolidin-3-yl]pentanoic acid, and wherein the species of the fungal cell is *Grosmannia clavigeru*. In an alternate embodiment, the present invention is a method for controlling bark beetle infestations of pine trees comprising contacting one or more fungal cells with an anti-fungal small molecule in an amount effective to reduce or inhibit conidial germination and mycelial growth, wherein the anti-fungal small molecule is either 5-(p-Bromobenzylidine)-α isopropyl-4-oxo-2-thioxo-3-thiozolidineacetic acid, 2-[5-(4-chlorobenzylidene)-4-oxo-2-thioxo-1,3-thiazolidin-3-yl]-3-methylbutanoic acid, 2-[5-(4-hydroxybenzylidene)-4-oxo-2-thioxo-1,3-thiazolidin-3-yl]pentanoic acid, [5-(4-isopropylbenzylidene)-4-oxo-2-thioxo-1,3-thiazolidin-3-yl] acetic acid or 2-[5-(2-chlorobenzylidene)-4-oxo-2-thioxo-1,3-thiazolidin-3-yl]pentanoic acid, and wherein the species of the fungal cell is *Ophiostoma montium*. In another alternate embodiment, the present invention is a method for controlling bark beetle infestations of pine trees comprising contacting one or more fungal cells with an anti-fungal small molecule in an amount effective to reduce or inhibit conidial germination and mycelial growth, wherein the anti-fungal small molecule is either 5-(p-Bromobenzylidine)-α-isopropyl-4-oxo-2-thioxo-3-thiozolidineacetic acid, 2-[5-(4-chlorobenzylidene)-4-oxo-2-thioxo-1,3-thiazolidin-3-yl]-3-methylbutanoic acid, 2-[5-(4-hydroxybenzylidene)-4-oxo-2-thioxo-1,3-thiazolidin-3-yl]pentanoic acid, [5-(4-isopropylbenzylidene)-4-oxo-2-thioxo-1,3-thiazolidin-3-yl] acetic acid or 2-[5-(2-chlorobenzylidene)-4-oxo-2-thioxo-1,3-thiazolidin-3-yl]pentanoic acid, and wherein the species of the fungal cell is *Ceratocystiopsis brevicomi*.

The present invention is a method for controlling conidial germination and mycelial growth in fungi comprising contacting a fungal cell with an anti-fungal small molecule in an amount effective to reduce or inhibit conidial germination and mycelial growth, wherein the anti-fungal small molecule is either 5-(p-Bromobenzylidine)-α-isopropyl-4-oxo-2-thioxo-3-thiozolidineacetic acid, 2-[5-(4-chlorobenzylidene)-4-oxo-2-thioxo-1,3-thiazolidin-3-yl]1-3-methylbutanoic acid, 2-[5-(4-hydroxybenzylidene)-4-oxo-2-thioxo-1,3-thiazolidin-3-yl]pentanoic acid, [5-(4-isopropylbenzylidene)-4-oxo-2-thioxo-1,3-thiazolidin-3-yl] acetic acid or 2-[5-(2-chlorobenzylidene)-4-oxo-2-thioxo-1,3-thiazolidin-3-yl]pentanoic acid, and wherein the species of the fungal cell is selected from a group that has an obligate symbiosis with the mountain pine beetle (*Dendroctonus ponderosae*) and the western pine beetle (*Dendroctonus bervicomis*). The present invention is also a method for controlling bark beetle infestations of pine trees comprising contacting one or more fungal cells with an anti-fungal small molecule in an amount effective to reduce or inhibit conidial germination and mycelial growth, wherein the anti-fungal small molecule is either 5-(p-Bromobenzylidine)-α-isopropyl-4-oxo-2-thioxo-3-thiozolidineacetic acid, 2-[5-(4-chlorobenzylidene)-4-oxo-2-thioxo-1,3-thiazolidin-3-yl]-3-methylbutanoic acid, 2-[5-(4-hydroxybenzylidene)-4-oxo-2-thioxo-1,3-thiazolidin-3-yl]pentanoic acid, [5-(4-isopropylbenzylidene)-4-oxo-2-thioxo-1,3-thiazolidin-3-yl] acetic acid or 2-[5-(2-chlorobenzylidene)-4-oxo-2-thioxo-1,3-thiazolidin-3-yl]pentanoic acid, and wherein the species of the fungal cell is selected from a group that has an obligate symbiosis with the mountain pine beetle (*Dendroctonus ponderosae*) and the western pine beetle (*Dendroctonus bervicomis*).

DETAILED DESCRIPTION OF INVENTION

A. Overview

Figure 1:
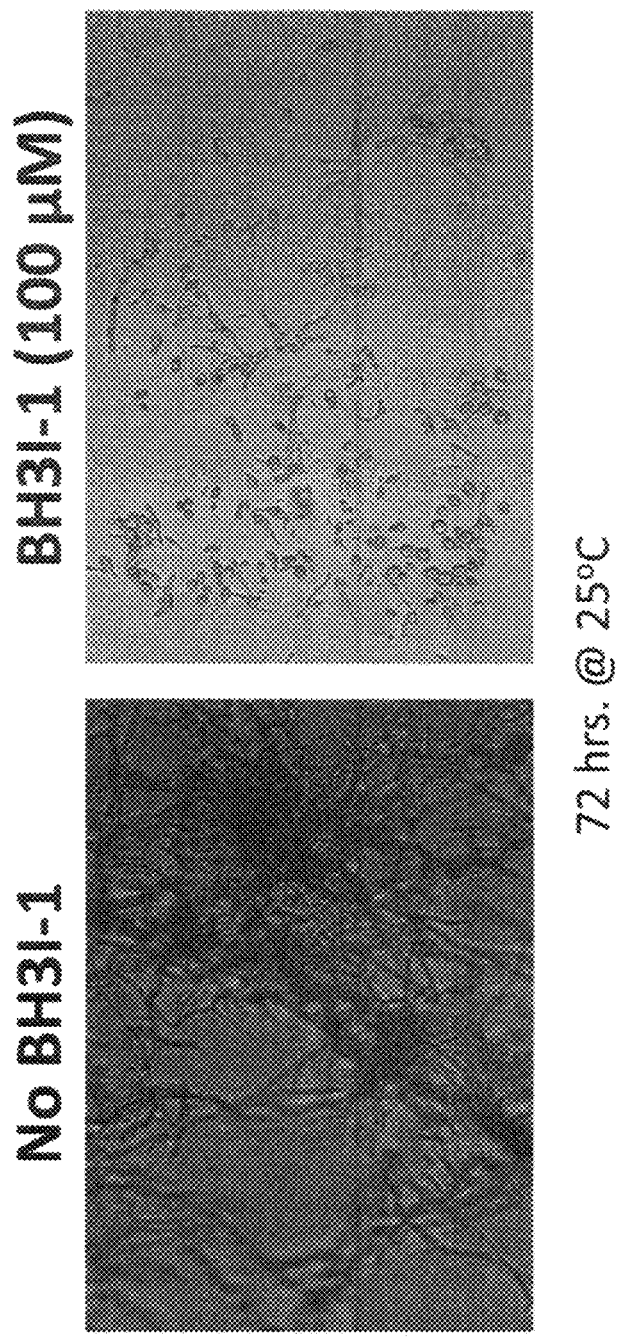
FIG. 1 shows *G. clavigera* grown in YNB (yeast nitrogen base) medium without BH3I-1 (left panel) and with 100 micromolar (µM) BH3I-1 (right panel) for 48 hours at 25° C. The number of cells inoculated is the same for each condition.

Currently very few options exist for controlling or limiting bark beetle infestations of coniferous trees. Chemical pesticides and beetle pheromone treatments are expensive and mostly ineffective. The present invention is based on the novel discovery of anti-fungal properties of the small molecules BH3I-1, BH3I-1-12, BH3I-1-66, BH3I-1-68 and BH3I-1-69 against *G. clavigera, O. montium* and *C. brevicomi*, obligate symbionts of the mountain pine beetle and western pine beetle. The invention provides a method for managing, controlling and/or limiting bark beetle infestations of coniferous trees through inhibition of conidial germination and mycelial growth of the fungi symbiotically associated with bark beetles.

B. Anti-Fungal Properties of BH3I-1, BH3I-1-12, BH3I-1-66, BH3I-1-68 and BH3I-1-69.

The inventors have discovered that the small molecule BH3I-1 and four derivatives of RH3I-1 are effective at inhibiting conidial germination and mycelial growth of *G. clavigera, O. montium* and *C. brevicomi*.

1. Assays for Inhibition of Conidial Germination and Mycelial Growth of Fungi We developed two different high-throughput assays to assess the anti-fungal activity of small organic molecules. Three fungal species symbiotically associated with bark beetles were used in these assays: *Grosmannia clavigera* (mountain pine beetle symbiont), *Ophiostoma montium* (mountain pine beetle symbiont) and *Ceratocystiopsis brevicomi* (western pine beetle symbiont).

In the first assay, referred to as the "microplate assay", fungi are first grown in liquid medium at 25° C. for 48 hours, and conidia are harvested by filtration through cheese cloth. The conidia are then transferred to the wells of an optical microplate containing (i) growth medium and (ii) varying concentrations of BH3I-1 (typically 0, 50, 100, 200 and 300 μM BH3I-1). The microplates are incubated for up to 120 hrs at 25° C. Germination and mycelial growth are monitored visually with a Nikon TE200 inverted microscope and spectrophotometrically in a Biotek Synergy H4 plate reader. For the spectrophotometric analysis, Optical Density 600 ($OD_{600}$) readings are taken every six hours over the course of the experiment.

The second assay is based on the standard "disk diffusion assay" routinely used in antimicrobial testing. Fungi are grown and harvested as for the microplate assay. After diluting 1:10, 150 μl of filtered conidia are spread evenly onto an Malt Extract Agar (MEA) plate. For each plate, 50 μg (0.12 μmole), 100 μg (0.25 μmole), 200 μg (0.50 μmole) and 300 μg (0.75 μmole) of the appropriate molecule (dissolved in DMSO) are spotted onto four separate Whatman Grade AA 6 mm filter disks. A control disk with 20 μl of DMSO only is also prepared. The DMSO is allowed to evaporate completely from each disk at room temperature and then the molecule-impregnated disks are positioned equidistant from each other on a plate. Plates are incubated at room temperature for 3 to 7 days, depending on the fungal species. At the end of the incubation period, the zone of inhibition (i.e., the region around each disk where no growth is visible) is measured from edge to edge of visible growth across and over the center of the disk. Images of the disk assays are obtained using an Epson Perfection V750 Pro desktop scanner.

2. Strains, Media and Chemicals

Strains of *G. clavigera, O. montium* and *C. brevicomi* were obtained from Dr. Diana Six at the University of Montana and maintained on MEA plates (see below) at room temperarture.

YPD medium (1% Yeast Extract, 2% Peptone and 2% Dextrose), a standard fungal growth medium, is used for these experiments. YPD plates included 1.5% agar.

MEA plates (1.275% Maltose, 0.275% Dextrin, 0.235% Glycerol, 0.078% Glucose, 1.5% agar).

Each small molecule was dissolved in dimethyl sulfoxide (DMSO) as a 10 mM stock and diluted directly into 100 μl of the appropriate YPD medium at 50 μM, 100 μM, 200 μM and 300 μM final concentration (for the microplate assay) or spotted onto Whatman 6 mm filter disks in 50 microgram (μg), 100 μg, 200 μg or 300 μg amounts (for the disk diffusion assay). The control condition (no small molecule) included DMSO to a concentration equivalent to that of the small molecule-containing wells or filter disks.

3. Results

Figure 2:
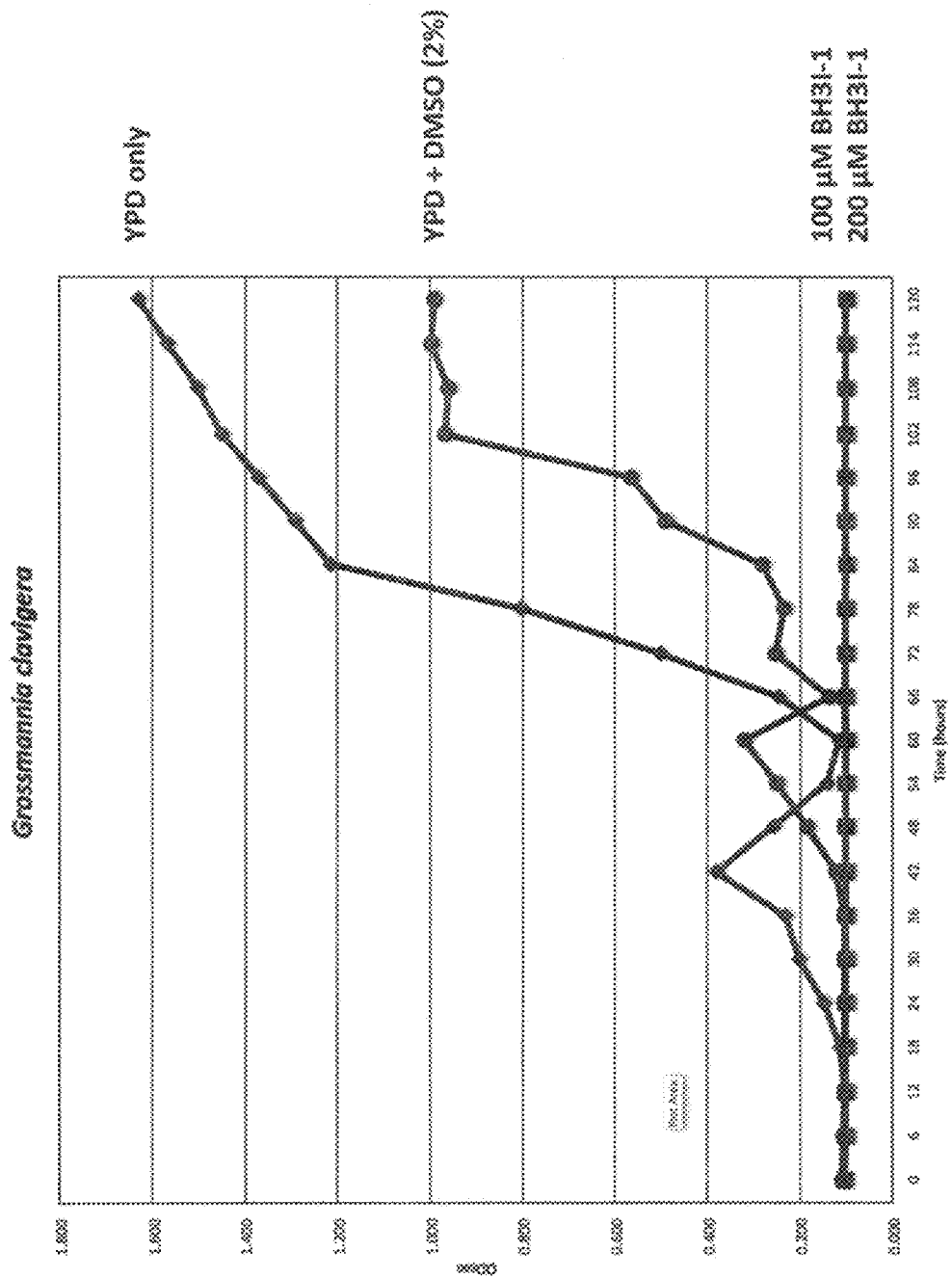
FIG. 2 shows growth curves for *G. clavigera* over 120 hours at 25° C. in YPD medium only, YPD plus DMSO and YPD with 100 µM and 200 µM BH3I-1.
Figure 3:
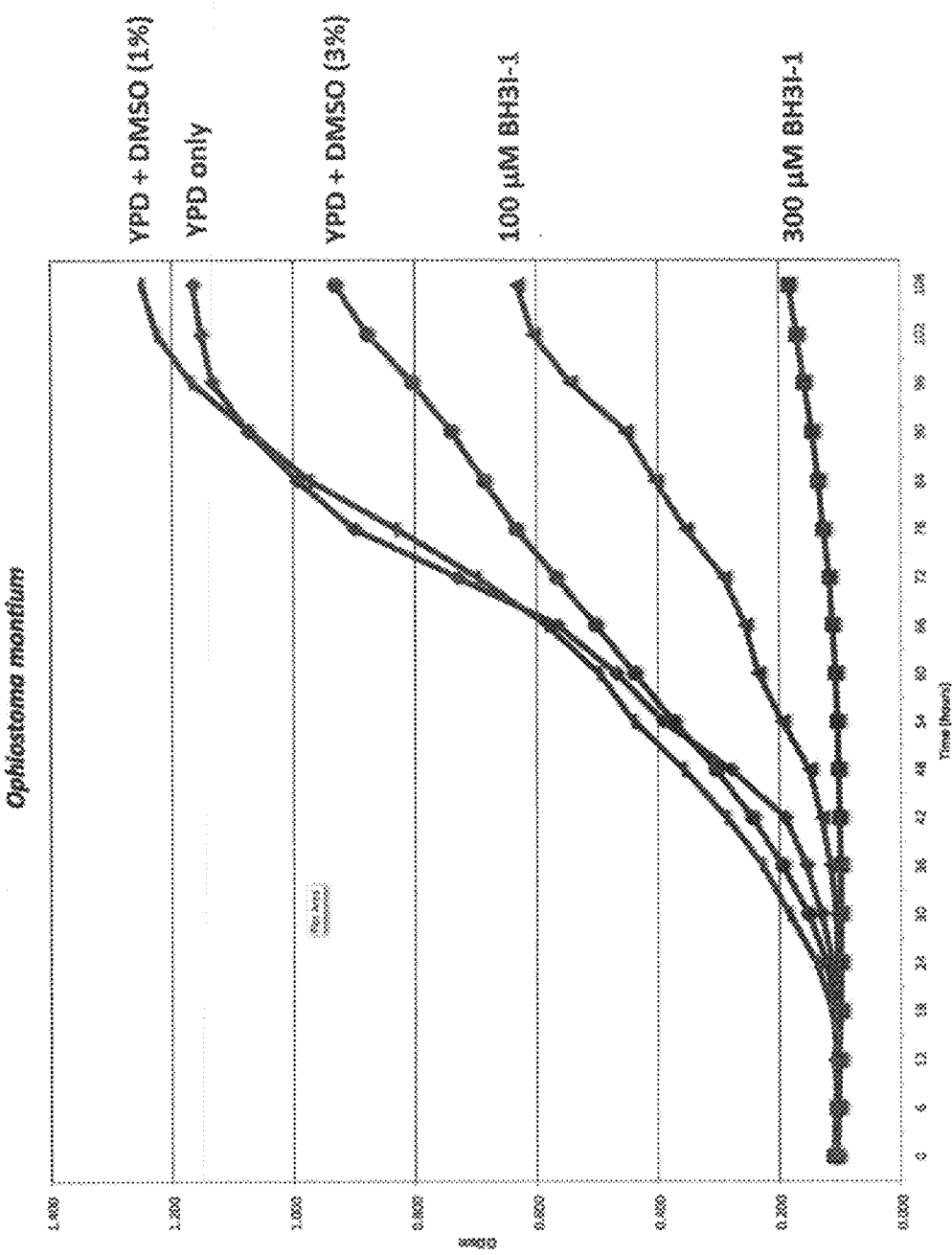
FIG. 3 shows growth curves for *O. montium* over 108 hours at 25° C. in YPD medium only, YPD plus DMSO and YPD with 100 µM and 300 µM BH3I-1.
Figure 4:
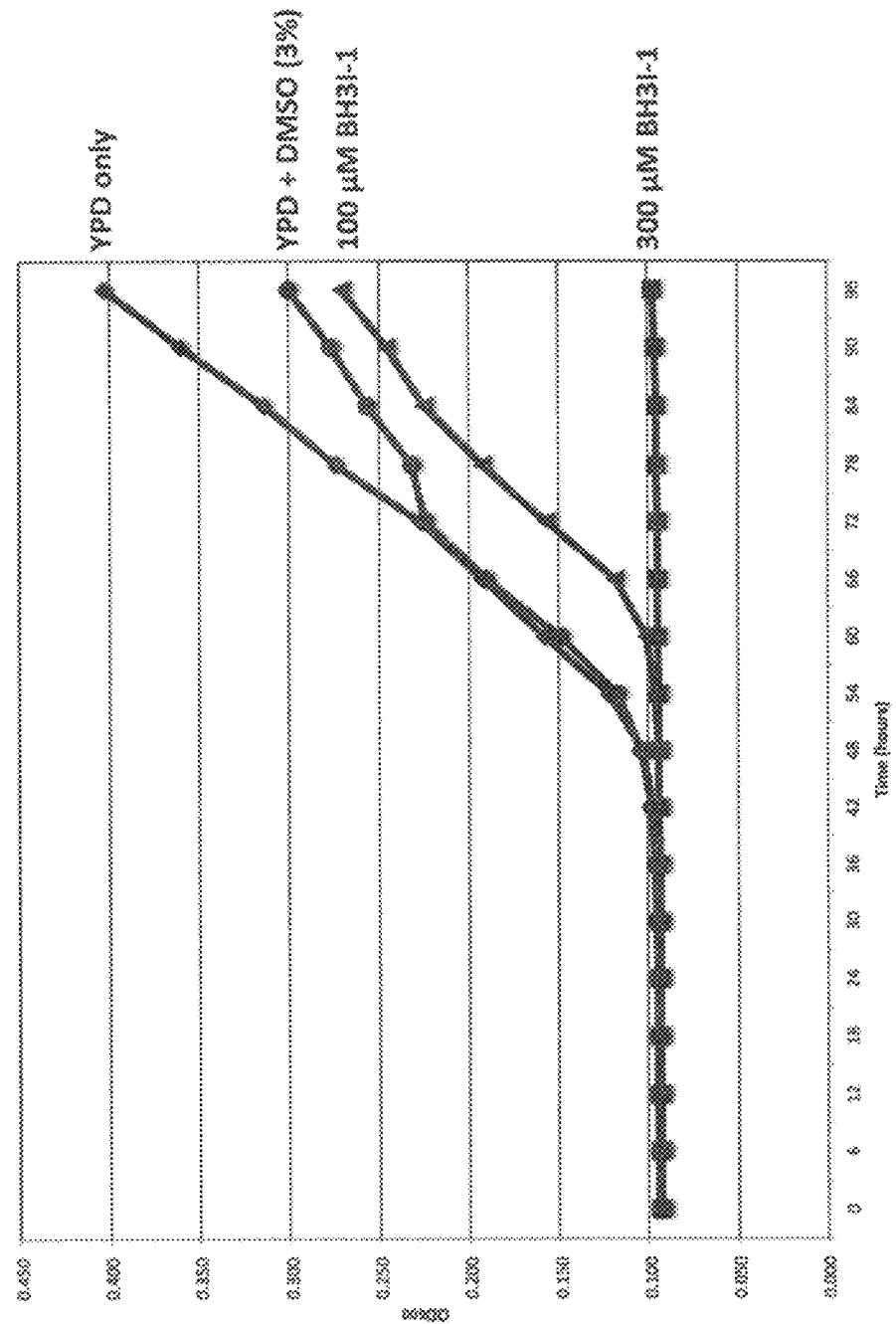
FIG. 4 shows growth curves for *C. brevicomi* over 96 hours at 25° C. in YPD medium only, YPD plus DMSO and YPD with 100 µM and 300 µM BH3I-1.
Figure 5:
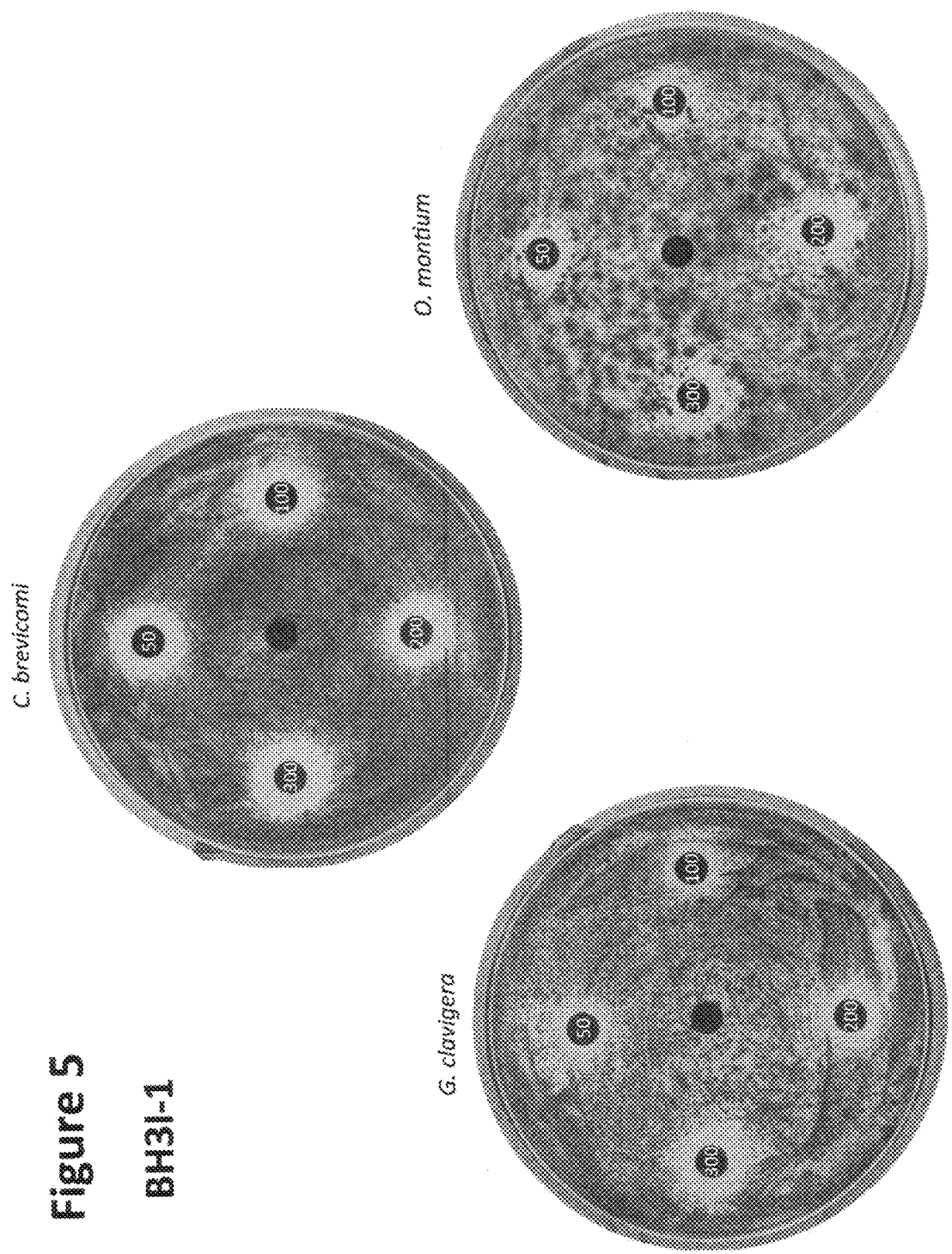
FIG. 5 shows a disk diffusion assay with BH3I-1 and *G. clavigera*, *C. brevicomi* and *O. montium*. Disks were impregnated with DMSO only as a negative control (the center disk on each plate), 50 microgram (µg), 100 µg, 200 µg and 300 µg BH3I-1.
Figure 6:
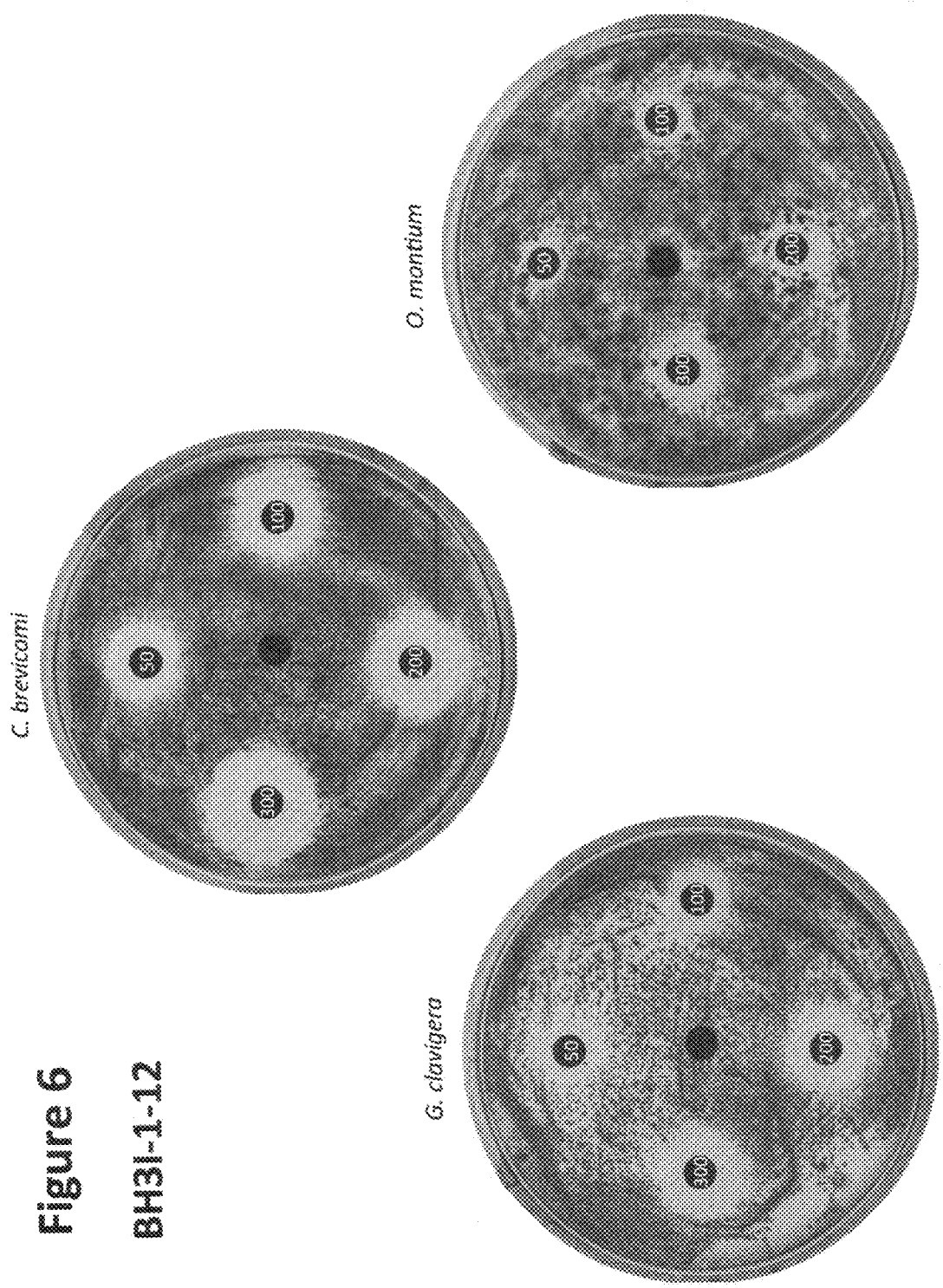
FIG. 6 shows a disk diffusion assay with BH3I-1-12 with *G. clavigera*, *C. brevicomi* and *O. montium*. Disks were impregnated with DMSO only as a negative control (the center disk on each plate), 50 µg, 100 µg, 200 µg and 300 µg BH3I-1-12.
Figure 7:
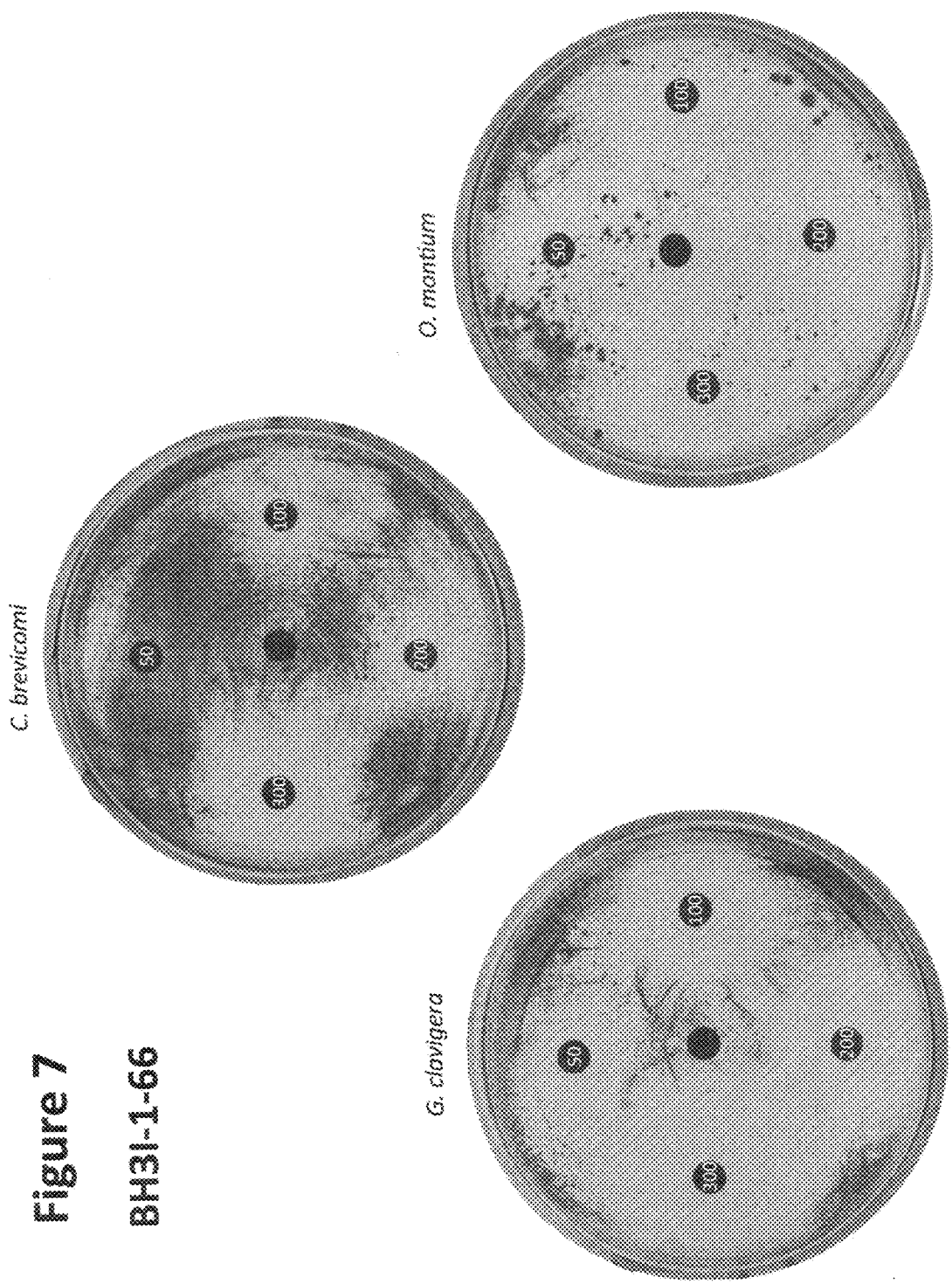
FIG. 7 shows a disk diffusion assay with BH3I-1-66 with *G. clavigera*, *C. brevicomi* and *O. montium*. Disks were impregnated with DMSO only as a negative control (the center disk on each plate), 50 µg, 100 µg, 200 µg and 300 µg BH3I-1-66.
Figure 8:
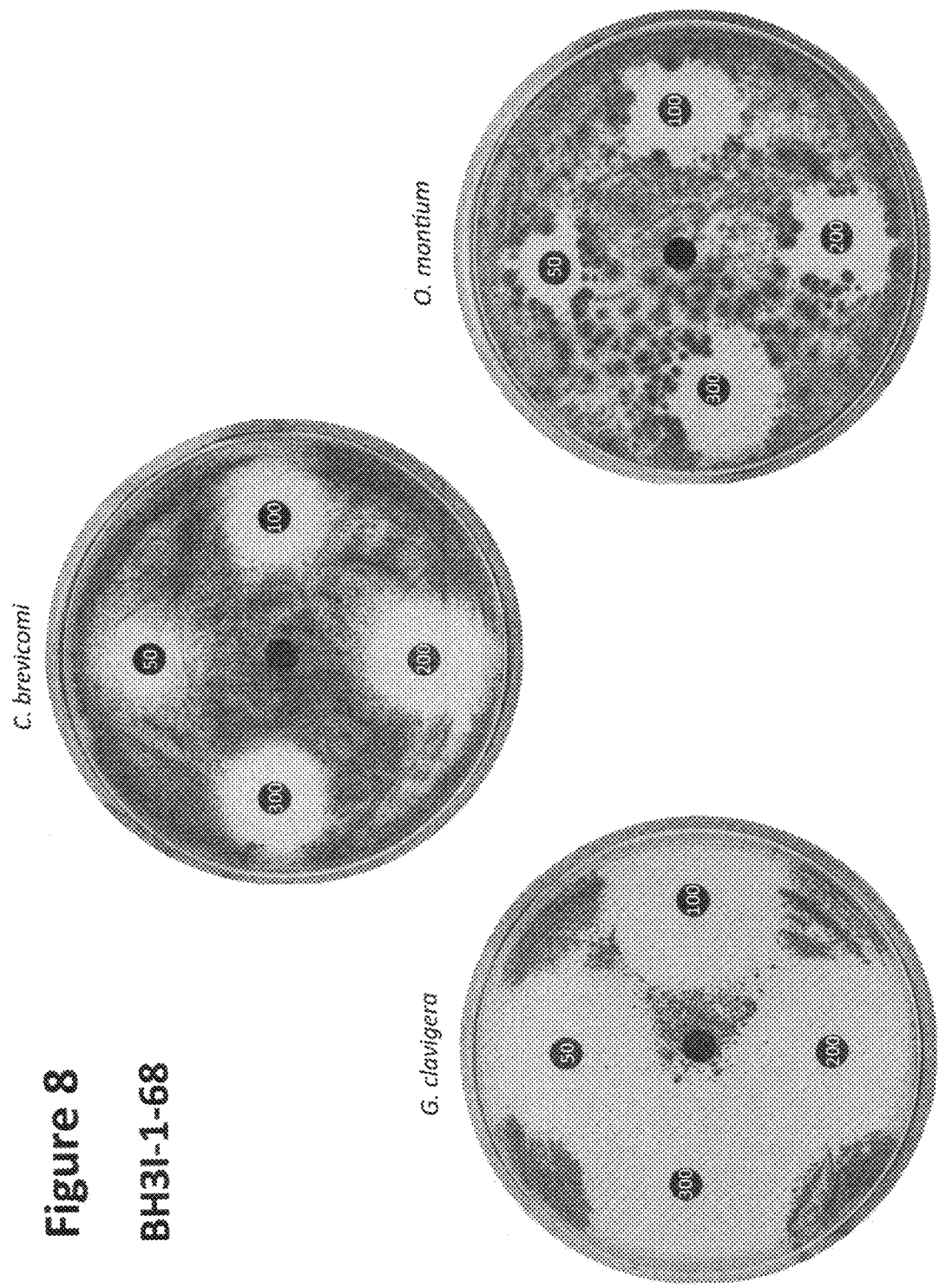
FIG. 8 shows a disk diffusion assay with BH3I-1-68 with *G. clavigera*, *C. brevicomi* and *O. montium*. Disks were impregnated with DMSO only as a negative control (the center disk on each plate), 50 µg, 100 µg, 200 µg and 300 µg BH3I-1-68.
Figure 9:
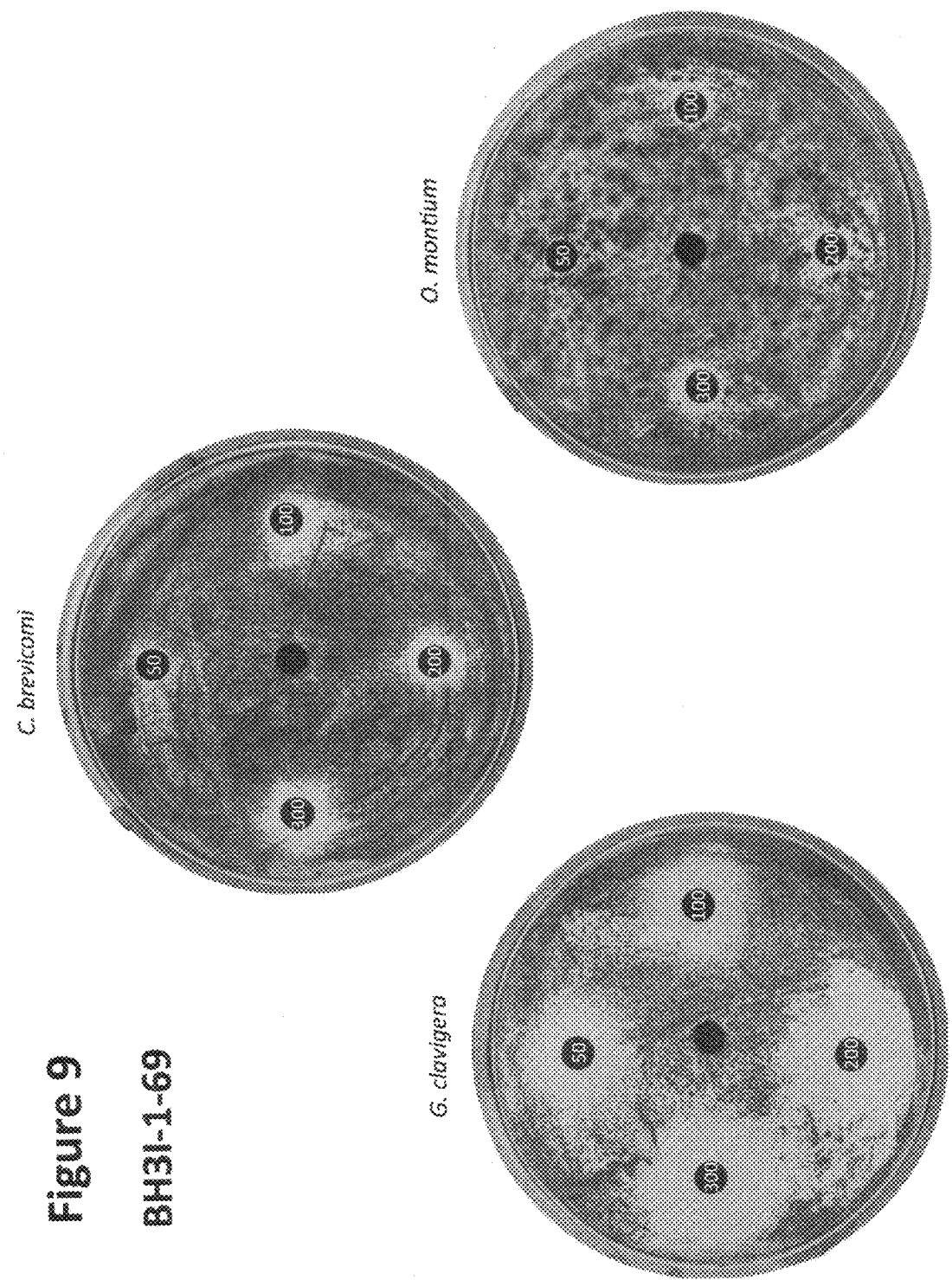
FIG. 9 shows a disk diffusion assay with BH3I-1-69 with *G. clavigera, C. brevicomi* and *O. montium*. Disks were impregnated with DMSO only as a negative control (the center disk on each plate), 50 μg, 100 μg, 200 μg and 300 μg BH3I-1-69.
Figure 10:
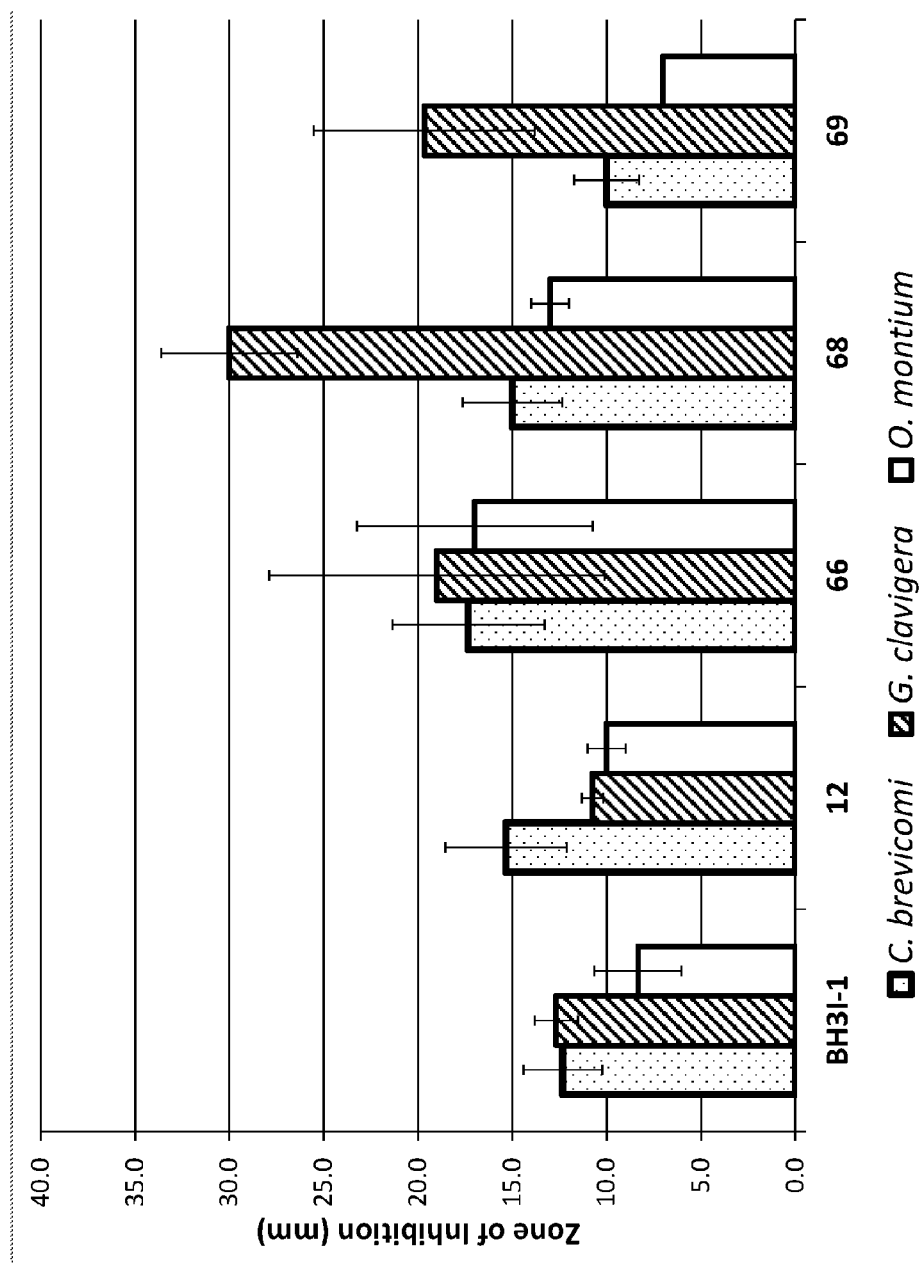
FIG. 10. Mean zone of inhibition for 200 μg per disk for three trials of BH3I-1, BH3I-1-12, BH3I-1-66, BH3I-1-68 and BH3I-1-69 against *G. clavigera, C. brevicomi* and *O. montium*. Bars represent standard deviation.

In the presence of 100 μM BH3I-1, approximately 80% of *G. clavigera* conidial cells failed to germinate. For those that did germinate, mycelia grew for a few hours and then stopped (FIG. 1). Growth inhibition was maintained for 120 hours (FIGS. 2 and 3). In contrast, without BH3I-1, *G. clavigera* conidia germinated and mycelial growth continued to confluence (FIGS. 1, 2 and 3). BH3I-1 also inhibited conidial germination and mycelial growth in *O. montium* and *C. brevicomi* (FIGS. 4 and 5).

In order to identify additional inhibitors of morphogenesis, we employed a core structure search of the Chembridge chemical database and identified 72 compounds of related structure to BH3I-1 (the "core structure" used in the database searches was defined as the benzylidene group attached to a thiazolidine ring). The BH3I-1-related molecules were tested in the disk diffusion assay (200 μg per disk) for anti-fungal activity against all three species of bark beetle-associated fungi. Of the 72 molecules tested, four showed promising anti-fungal activity against all the three fungal species. These molecules were retested three separate times with 50, 100, 200 and 300 µg per disk (FIGS. 6, 7, 8, 9, 10).

C. Structure of BH3I-1, BH3I-1-12, BH3I-1-66, BH3I-1-68 and BH3I-1-69.

Figure 11:
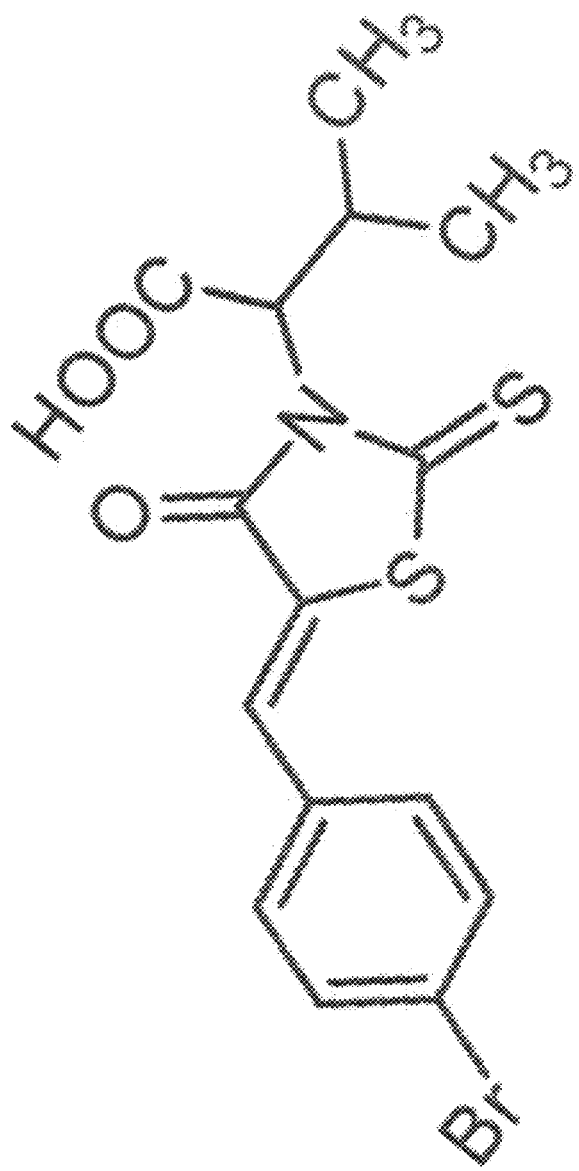
FIG. 11 shows a schematic representation of the chemical structure of BH3I-1 (5-(p-Bromobenzylidine)-α-isopropyl-4-oxo-2-thioxo-3-thiozolidineacetic acid).
Figure 12:
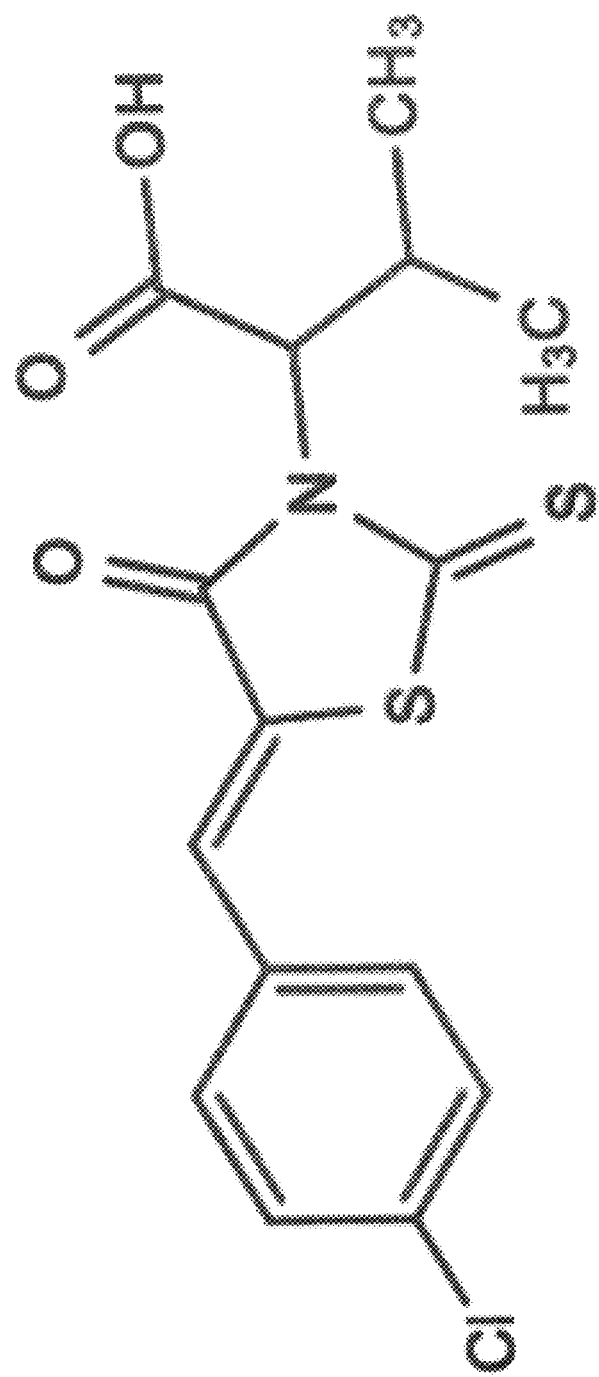
FIG. 12 is a schematic representation of the chemical structure of BH3I-1-12 (2-[5-(4-chlorobenzylidene)-4-oxo-2-thioxo-1,3-thiazolidin-3-yl]-3-methylbutanoic acid).
Figure 13:
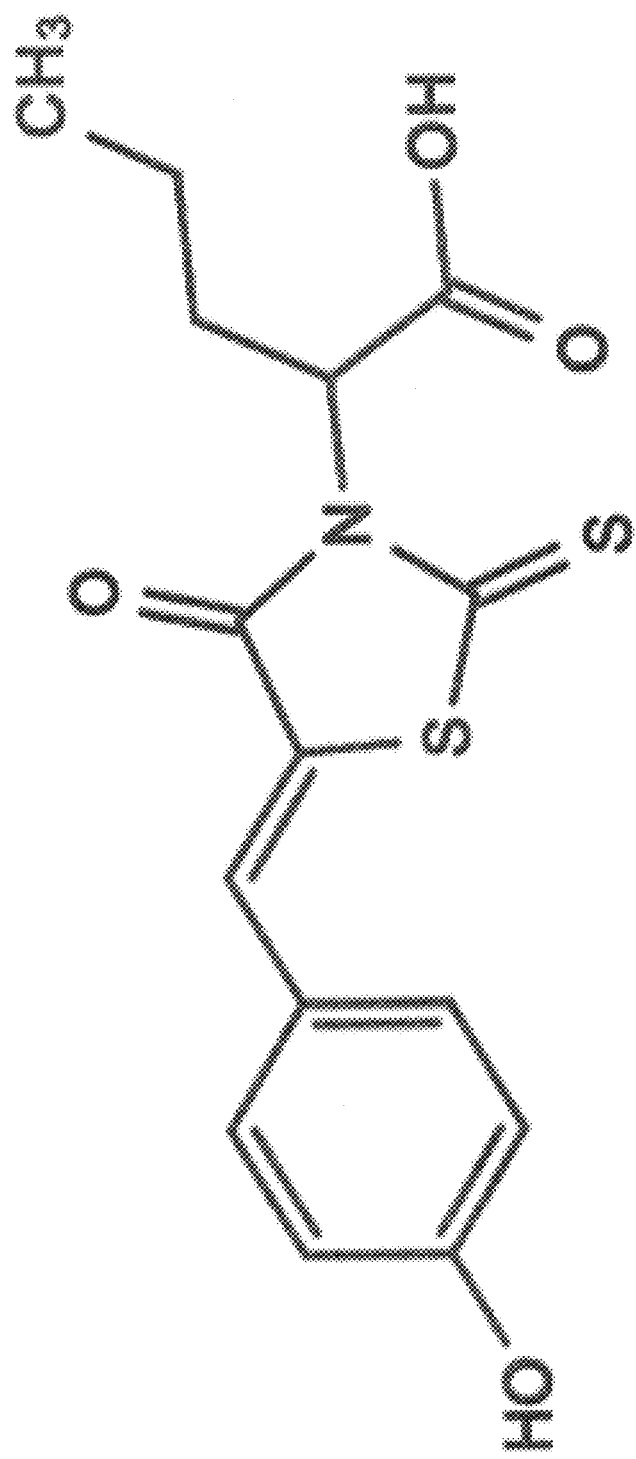
FIG. 13 is a schematic representation of the chemical structure of BH3I-1-66 (2-[5-(4-hydroxybenzylidene)-4-oxo-2-thioxo-1,3-thiazolidin-3-yl]pentanoic acid).
Figure 14:
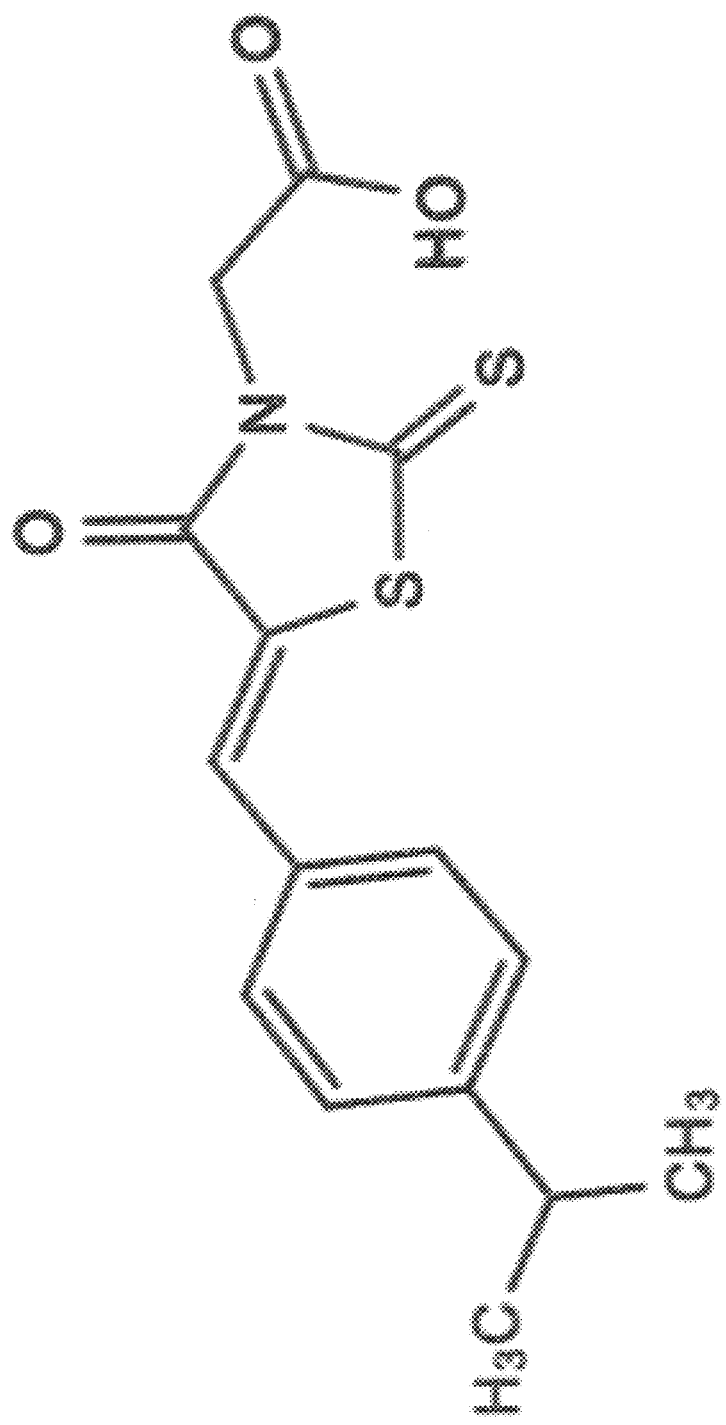
FIG. 14 is a schematic representation of the chemical structure of BH3I-1-68 ([5-(4-isopropylbenzylidene)-4-oxo-2-thioxo-1,3-thiazolidin-3-yl]acetic acid).
Figure 15:
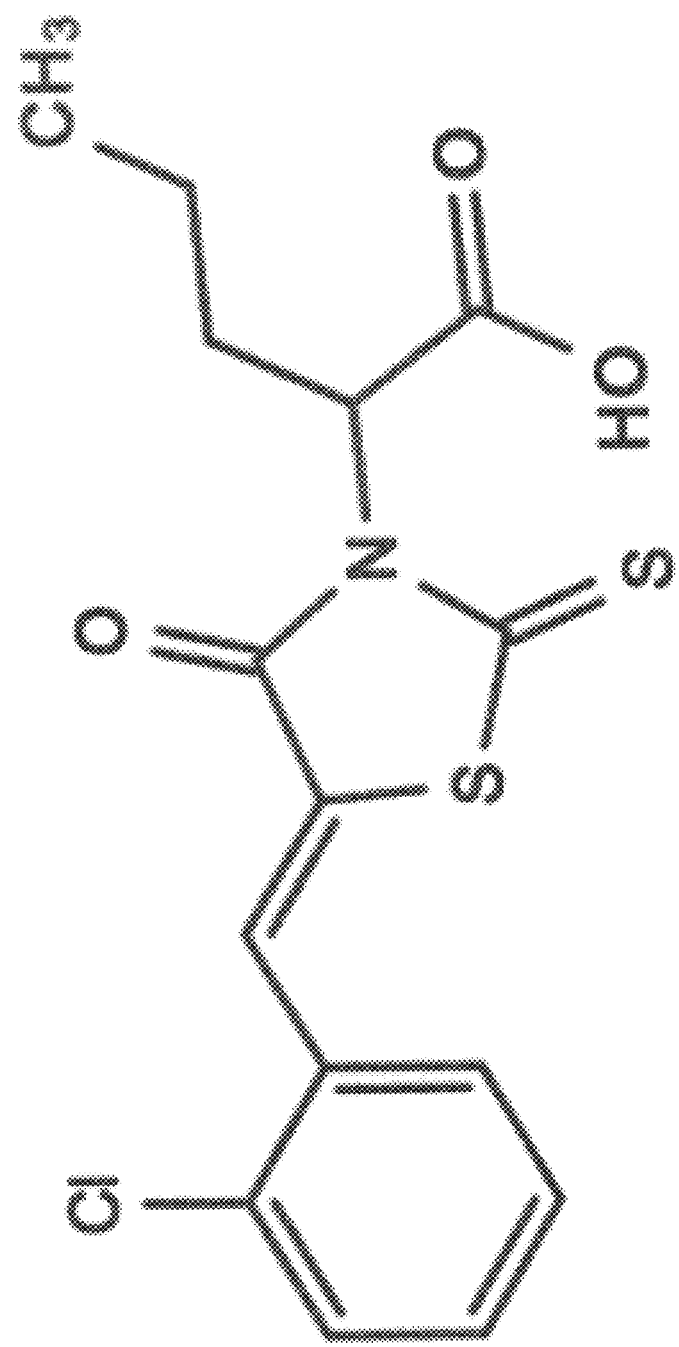
FIG. 15 is a schematic representation of the chemical structure of BH3I-1-69 (2-[5-(2-chlorobenzylidene)-4-oxo-2-thioxo-1,3-thiazolidin-3-yl]pentanoic acid).

The antifungal small molecule BH3I-1 (5-(p-Bromobenzylidene)-α-isopropyl-4-oxo-2-thioxo-3-thiozolidineacetic acid) has the chemical structure shown in FIG. 11. The antifungal small molecule BH3I-1-12 (2-[5-(4-chlorobenzylidene)-4-oxo-2-thioxo-1,3-thiazolidin-3-yl]-3-methylbutanoic acid) has the chemical structure shown in FIG. 12. The antifungal small molecule BH3I-1-66 (2-[5-(4-hydroxybenzylidene)-4-oxo-2-thioxo-1,3-thiazolidin-3-yl]pentanoic acid) has the chemical structure shown in FIG. 13. The antifungal small molecule BH3I-1-68 ([5-(4-isopropylbenzylidene)-4-oxo-2-thioxo-1,3-thiazolidin-3-yl]acetic acid) has the chemical structure shown in FIG. 14. The antifungal small molecule BH3I-1-69 (2[5-(2-chlorobenzylidene)-4-oxo-2-thioxo-1,3-thiazolidin-3-yl]pentanoic acid) has the chemical structure shown in FIG. 15.

According to some aspects of the invention, the BH3I-1, BH3I-1-12, BH3I-1-66, BH3I-1-68 and BH3I-1-69 molecules used in the methods for inhibiting conidial germination and mycelial growth of fungi may be used as a substantially isomerically-pure compound or as a mixture of isomers. Preferably, isomerically-pure compounds are used. Isomerically-pure, as used herein, means that one isomer will be present in an amount ranging from 51 to 100%, but not with respect to other impurities or other compounds that may be present. The term "isomer," as used herein, may refer to an E or Z isomer, an R or S isomer, an enantiomer or a diastereomer.

D. Practical Applications

BH3I-1, BH3I-1-12, BH3I-1-66, BH3I-1-68 and BH3I-1-69 are useful for a variety of in vitro and in situ applications. In one application of the present invention, a fungal cell is contacted with BH3I-1, BH3I-1-12, BH3I-1-66, BH3I-1-68 or BH3I-1-69 in an amount effective to reduce or inhibit conidial germination and/or mycelial growth. It is intended that the fungal cell is contacted either in vitro or in situ, whereby in situ includes contacting a fungal cell on the surface of or within a bark beetle. One of ordinary skill in the art would understand "contacting" to encompass putting a fungal cell into contact with BH3I-1, BH3I-1-12, BH3I-1-66, BH3I-1-68 or BH3I-1-69, for example, in a culture plate or flask, whereby the fungal cell is placed into media containing BH3I-1, BH3I-1-12, BH3I-1-66, BH3I-1-68 or BH3I-1-69. Further "contacting" would be understood by one of ordinary skill in the art to mean adding BH3I-1, BH3I-1-12, BH3I-1-66, BH3I-1-68 or BH3I-1-69 to a fungal cell or population of fungal cells on the surface of or within a bark beetle.

As used herein, the term "fungal cell" is intended to encompass any cell originating from a fungal species or fungus. As used herein, the term "fungus" includes molds, yeast and pathogenic yeast. A fungus includes, but is not limited to, *Grosmannia* (for example, *Grosmannia clavigera*), *Ophiostoma* (for example, *Ophiostoma montium, Ophiostoma ips*) and *Ceratocystiopsis* (for example, *Ceratocystiopsis brevicomi*).

Although the invention has been described in connection with specific embodiments and applications thereof, the invention is capable of further modifications and/or applications, and this application is intended to cover any and all variations, uses, or adaptations of the invention that fall within the scope of the invention as described herein. The appended claims are therefore intended to cover all such variations, uses and adaptations as fall within the true spirit and scope of the invention.

REFERENCES

1. Six, D. (2012) Ecological and evolutionary determinants of bark beetle-fungus symbioses. Insects 3: 339-366.
2. Six, D. L. and T. D. Paine (1998) The effects of mycangial fungi on development and emergence of *Dendroctonus ponderosae* and *D. jeffreyi*. Environmental Entomology. 27: 1393-1401.
3. Blciker, K. and D. L. Six (2007) Dietary benefits of fungal associates to an eruptive herbivore: potential implications of multiple associates on host population dynamics. Environmental Entomology 36: 1384-1396.
4. Six, D. L. and M. J. Wingfield (2011) The Role of Phytopathogenicity in Bark Beetle-Fungus Symbioses: A Challenge to the Classic Paradigm. Annu. Rev. Entomol. 56: 255-272.
5. U.S. Patent No. RE43,615 (Toenjes, 2012) Method for controlling the yeast-to-filamentous growth transition in fungi.
6. DiGuistini et al. (2011) Genome and transcriptome analyses of the mountain pine beetle-fungal symbiont *Grosmannia clavigera*, a lodgepole pine pathogen. Proc. Natl. Academ. Sci. 108(6): 2504-2509.
7. Galagan, J. E., Henn, M. R., Ma, L., Cuomo, C. A., and B. Birren (2005) Genomics of the fungal kingdom: insights into eukaryotic biology. Genome Research. 15(12): 1620-1631.
8. Schmalreck et al. (2014) Phylogenetic relationships matter: antifungal susceptibility among clinically relevant yeasts. Antimicrobial Agents and Chemotherapy. 58(3): 1575-1585.

We claim:

1. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(4-chlorobenzylidene)-4-oxo-2-thioxo-1,3-thiazolidin-3-yl]-3-methylbutanoic acid, and wherein the species of the fungal cell is *Grosmannia clavigera*.

2. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(4-chlorobenzylidene)-4-oxo-2-thioxo-1,3-thiazolidin-3-yl]-3-methylbutanoic acid, and wherein the species of the fungal cell is *Ophiostoma montium*.

3. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(4-chlorobenzylidene)-4-oxo-2-thioxo-1,3-thiazolidin-3-yl]-3-methylbutanoic acid, and wherein the species of the fungal cell is *Ceratocystiopsis brevicomi*.

4. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(4-chlorobenzylidene)-4-oxo-2-thioxo-1,3-thiazolidin-3-yl]-3- methylbutanoic acid, and wherein the species of the fungal cell is *Grosmannia clavigera*.

5. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(4-chlorobenzylidene)-4-oxo-2-thioxo-1,3-thiazolidin-3-yl]-3-methylbutanoic acid, and wherein the species of the fungal cell is *Ophiostoma montium*.

6. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(4-chlorobenzylidene)-4-oxo-2-thioxo-1,3-thiazolidin-3-yl]-3-methylbutanoic acid, and wherein the species of the fungal cell is *Ceratocystiopsis brevicomi*.

7. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(4-chlorobenzylidene)-4-oxo-2-thioxo-1,3-thiazolidin-3-yl]-3-methylbutanoic acid, and wherein the species of the fungal cell is selected from a group that has an obligate symbiosis with the mountain pine beetle (*Dendroctonus ponderosae*) and the western pine beetle (*Dendroctonus bervicomis*).

8. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(4-chlorobenzylidene)-4-oxo-2-thioxo-1,3-thiazolidin-3-yl]-3-methylbutanoic acid, and wherein the species of the fungal cell is selected from a group that has an obligate symbiosis with the mountain pine beetle (*Dendroctonus ponderosae*) and the western pine beetle (*Dendroctonus bervicomis*).

9. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(4-hydroxybenzylidene)-4-oxo-2-thioxo-1,3-thiazolidin-3-yl]pentanoic acid, and wherein the species of the fungal cell is *Grosmannia clavigera*.

10. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(4-hydroxybenzylidene)-4-oxo-2-thioxo-1,3-thiazolidin-3-yl]pentanoic acid, and wherein the species of the fungal cell is *Ophiostoma montium*.

11. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(4-hydroxybenzylidene)-4-oxo-2-thioxo-1,3-thiazolidin-3-yl]pentanoic acid, and wherein the species of the fungal cell is *Ceratocystiopsis brevicomi*.

12. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(4-hydroxybenzylidene)-4-oxo-2-thioxo-1,3-thiazolidin-3-yl]pentanoic acid and wherein the species of the fungal cell is *Grosmannia clavigera*.

13. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(4-hydroxybenzylidene)-4-oxo-2-thioxo-1,3-thiazolidin-3-yl]pentanoic acid, and wherein the species of the fungal cell is *Ophiostoma montium*.

14. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(4-hydroxybenzylidene)-4-oxo-2-thioxo-1,3-thiazolidin-3-yl]pentanoic acid, and wherein the species of the fungal cell is *Ceratocystiopsis brevicomi*.

15. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(4-hydroxybenzylidene)-4-oxo-2-thioxo-1,3-thiazolidin-3-yl]pentanoic acid, and wherein the species of the fungal cell is selected from a group that has an obligate symbiosis with the mountain pine beetle (*Dendroctonus ponderosae*) and the western pine beetle (*Dendroctonus bervicomis*).

16. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(4-hydroxybenzylidene)-4-oxo-2-thioxo-1,3-thiazolidin-3-yl]pentanoic acid, and wherein the species of the fungal cell is selected from a group that has an obligate symbiosis with the mountain pine beetle (*Dendroctonus ponderosae*) and the western pine beetle (*Dendroctonus bervicomis*).

17. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is [5-(4-isopropyl-benzylidene)-4-oxo-2-thioxo-1,3-thiazolidin-3-yl]acetic acid, and wherein the species of the fungal cell is *Grosmannia clavigera*.

18. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is [5-(4-isopropyl-benzylidene)-4-oxo-2-thioxo-1,3-thiazolidin-3-yl]acetic acid, and wherein the species of the fungal cell is *Ophiostoma montium*.

19. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is [5-(4-isupropyl-benzylidene)-4-oxo-2-thioxo-1,3-thiazolidin-3-yl]acetic acid, and wherein the species of the fungal cell is *Ceratocystiopsis brevicomi*.

20. A method for controlling bark beetle infestations of pine trees comprising contacting one or more fungal cells with an anti-fungal small molecule in an amount effective to reduce or inhibit conidial germination and mycelial growth, wherein the anti-fungal small molecule is [5-(4-isopropyl-benzylidene)-4-oxo-2-thioxo-1,3-thiazolidin-3-yl]acetic acid, and wherein the species of the fungal cell is *Grosmannia clavigera*.

21. A method for controlling bark beetle infestations of pine trees comprising contacting one or more fungal cells with an anti-fungal small molecule in an amount effective to reduce or inhibit conidial germination and mycelial growth, wherein the anti-fungal small molecule is [5-(4-isopropyl-benzylidene)-4-oxo-2-thioxo-1,3-thiazolidin-3-yl]acetic acid, and wherein the species of the fungal cell is *Ophiostoma montium*.

22. A method for controlling bark beetle infestations of pine trees comprising contacting one or more fungal cells with an anti-fungal small molecule in an amount effective to reduce or inhibit conidial germination and mycelial growth, wherein the anti-fungal small molecule is [5-(4-isopropyl-benzylidene)-4-oxo-2-thioxo-1,3-thiazolidin-3-yl]acetic acid, and wherein the species of the fungal cell is *Ceratocystiopsis brevicomi*.

23. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is [5-(4-isopropyl-benzylidene)-4-oxo-2-thioxo-1,3-thiazolidin-3-yl]acetic acid, and wherein the species of the fungal cell is selected from a group that has an obligate symbiosis with the mountain pine beetle (*Dendroctonus ponderosae*) and the western pine beetle (*Dendroctonus bervicomis*).

24. A method for controlling bark beetle infestations of pine trees comprising contacting one or more fungal cells with an anti-fungal small molecule in an amount effective to reduce or inhibit conidial germination and mycelial growth, wherein the anti-fungal small molecule is [5-(4-isopropyl-benzylidene)-4-oxo-2-thioxo-1,3-thiazolidin-3-yl]acetic acid, and wherein the species of the fungal cell is selected from a group that has an obligate symbiosis with the mountain pine beetle (*Dendroctonus ponderosas*) and the western pine beetle (*Dendroctonus bervicomis*).

25. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(2-chlorobenzylidene)-4-oxo-2-thioxo-1,3-thiazolidin-3-yl]pentanoic acid, and wherein the species of the fungal cell is *Grosmannia clavigera*.

26. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(2-chlorobenzylidene)-4-oxo-2-thioxo-1,3-thiazolidin-3-yl]pentanoic acid, and wherein the species of the fungal cell is *Ophiostoma montium*.

27. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(2-chlorobenzylidene)-4-oxo-2-thioxo-1,3-thiazolidin-3-yl]pentanoic acid, and wherein the species of the fungal cell is *Ceratocystiopsis brevicomi*.

28. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(2-chlorobenzylidene)-4-oxo-2-thioxo-1,3-thiazolidin-3-yl]pentanoic acid, and wherein the species of the fungal cell is *Grosmannia clavigera*.

29. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(2-chlorobenzylidene)-4-oxo-2-thioxo-1,3-thiazolidin-3-yl]pentanoic acid, and wherein the species of the fungal cell is *Ophiostoma montium*.

30. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(2-chlorobenzylidene)-4-oxo-2-thioxo-1,3-thiazolidin-3-yl]pentanoic acid, and wherein the species of the fungal cell is *Ceratocystiopsis brevicomi*.

31. A method for controlling conidial germination and mycelial growth in fungi comprising contacting a fungal cell with an anti-fungal small molecule in an amount effective to reduce or inhibit conidial germination and mycelial growth, wherein the anti-fungal small molecule is 2-[5-(2-chlorobenzylidene)-4-oxo-2-thioxo-1,3-thiazolidin-3-yl]pentanoic acid, and wherein the species of the fungal cell is selected from a group that has an obligate symbiosis with the mountain pine beetle (*Dendroctonus ponderosae*) and the western pine beetle (*Dendroctonus bervicomis*).

32. A method for controlling bark beetle infestations of pine trees comprising contacting one or more fungal cells with an anti-fungal small molecule in an amount effective to reduce or inhibit conidial germination and mycelial growth, wherein the anti-fungal small molecule is 2-[5-(2-chlorobenzylidene)-4-oxo-2-thioxo-1,3-thiazolidin-3-yl]pentanoic acid, and wherein the species of the fungal cell is selected from a group that has an obligate symbiosis with the mountain pine beetle (*Dendroctonus ponderosae*) and the western pine beetle (*Dendroctonus bervicomis*).

\* \* \* \* \*